United States Patent [19]

Turner

[11] Patent Number: 5,540,913
[45] Date of Patent: * Jul. 30, 1996

[54] FORMULATIONS AND USES THEREOF IN THE PREVENTION AND TREATMENT OF ORAL LESIONS

[76] Inventor: Robert E. Turner, 209 Dewey Dr. #2, New Kensington, Pa. 15068

[*] Notice: The term of this patent shall not extend beyond the expiration date of Pat. No. 5,276,216.

[21] Appl. No.: 233,918

[22] Filed: Apr. 26, 1994

Related U.S. Application Data

[63] Continuation-in-part of Ser. No. 766,365, Sep. 25, 1991, Pat. No. 5,296,216, which is a continuation of Ser. No. 423,500, Oct. 12, 1989, Pat. No. 5,306,509, which is a continuation of Ser. No. 26,738, Mar. 17, 1987, abandoned.

[51] Int. Cl.$^6$ ............... A61K 7/16; A61K 7/20; A61K 33/10

[52] U.S. Cl. ............... 424/53; 424/49; 424/717; 424/680; 424/616; 424/613; 514/714; 514/900; 514/901; 514/902

[58] Field of Search ............... 424/49–58

[56] References Cited

U.S. PATENT DOCUMENTS

| | | | |
|---|---|---|---|
| 3,729,553 | 4/1973 | Gold et al. | 424/44 |
| 4,024,237 | 5/1977 | Eichel et al. | 424/49 |
| 4,132,770 | 1/1979 | Barth | 424/49 |
| 4,250,168 | 2/1981 | Crawford | 424/127 |
| 4,606,912 | 8/1986 | Rudy et al. | 424/52 |
| 4,776,500 | 10/1988 | Ford | 222/402.1 |
| 4,868,161 | 9/1989 | Roberts | 514/49 |
| 4,971,782 | 11/1990 | Rudy et al. | 424/53 |
| 5,008,106 | 4/1991 | Merianos et al. | 424/80 |
| 5,039,515 | 8/1991 | Korf | 424/53 |
| 5,104,644 | 4/1992 | Douglas | 424/53 |
| 5,296,216 | 3/1994 | Turner | 424/53 |
| 5,306,509 | 4/1994 | Turner | 424/616 |

FOREIGN PATENT DOCUMENTS 944506  4/1949  France .

OTHER PUBLICATIONS

Sonis, Stephen T., "Epidemiology, Frequency, Distribution, Mechanisms, and Histopathology", *Oral Complications of Cancer Chemotherapy*, Peterson and Sonis, Eds., Martinus Nijhoff Publishers, Boston, Mass., Chapter 1, pp. 1–4, 1990.

Amigoni, N. A. et al J Am Dent Assoc 114(2) 217–221 Feb. 1987.

Herrin J R et al J Am Dent Assoc 113(4):607–611 Oct. 1986.

Slots J et al J Clin Periodontol 12(7);540–542 Aug. 1985.

Rosling B G et al. J. Clin Periodontol 10(5):487–514 Sep. 1983.

Herrin J. R. J. Periodontol 58(11):785–788 (1987).

Pihlstrom B et al J. Periodontol 58(5):291–300 (1987).

Wolff L. F. et al J. Periodontol 58(5): 301–307 (1987).

Bakdash, M. B. et al J. Periodontol 58(5):308–313 (1987).

*Primary Examiner*—Shep K. Rose
*Attorney, Agent, or Firm*—Arnold, White & Durkee

[57] ABSTRACT

The present invention provides compositions in the form of solutions, tablets and gels adapted for prophylaxis and treatment of oral lesions. The compositions are suitable for use as an oral lavage, and comprises water, a peroxide (preferably hydrogen peroxide) in a premixed aqueous form in the preparation mixture, with between about 0.01% and about 0.4% of a bicarbonate (preferably sodium bicarbonate). To produce such a composition adapted for the prophylaxis and treatment of oral lesions most preferably involves dissolving the peroxide and bicarbonate in an aqueous solution to produce a premixed preparation. Additionally, a method for prophylaxis and treatment of oral lesions incident the use of chemotherapeutic agents is included in the present invention.

12 Claims, No Drawings

FORMULATIONS AND USES THEREOF IN THE PREVENTION AND TREATMENT OF ORAL LESIONS

This application is a continuation-in-part application of U.S. Ser. No. 07/766,365 filed Sep. 25, 1991, now U.S. Pat. No. 5,296,216. U.S. patent application Ser. No. 07/766,365 is a continuation of U.S. patent application Ser. No. 07/423,500 filed Oct. 12, 1989 (now U.S. Pat. No. 5,306,509), which is a file wrapper continuation of U.S. patent application Ser. No. 07/026,738 filed Mar. 17, 1987, now abandoned.

BACKGROUND OF THE INVENTION

1. Field of the Invention

The present invention relates to the field of oral rinses and therapeutic formulations. The invention also relates to methods of preparing and using such formulations, for example in the maintenance of oral health. Methods for treating oral pathologies, including the types of oral pathologies that afflict persons with depresseded immune systems, such as persons undergoing chemotherapy, are also disclosed. The present invention also relates to a composition and method of prophylaxis and treatment for oral mucosal lesions.

2. Description of the Related Art

Oral lesions of various forms may develop in many circumstances and conditions. These forms of oral lesions include, for example, ulcerations, infections, stomatitis and vesiculo-bullous lesions. Among the most acute of these oral lesions are those typically occurring as an incident to cancer chemotherapy. These chemotherapy-related lesions may be so painful and severe as to force cessation of the chemotherapy, as well as eating and drinking, which may interfere with medical treatment. The lack of a consistent, effective and convenient method of prophylaxis and treatment for such oral lesions has too long been a therapeutic handicap.

Certain antineoplastic drugs have well documented direct and indirect stomatotoxicity. The direct toxicity is characterized by the interruption of the migrating, maturing squamous cells from the basal cell layer to the oral mucosal surface. As this normal progression is attenuated and desquamation of surface cells continues, it may be clinically manifested as oral mucosal ulcerations. Acute and severe pain may be associated with this ulcerative process at it's developmental peak. Patients have discontinued their chemotherapy due to this complication. Such cessation means that the full chemotherapy protocol cannot be delivered and thus, the patient may not be provided the best therapeutic effect. Control or cure of the cancer may be lost. The patient and family are then placed in an emotional struggle between gaining relief from the oral pain and simultaneously realizing that in doing so the cancer may continue to progress.

The indirect stomatotoxic effects are related to alteration of the hematologic status through myelosuppression and the patient's subsequent decreased ability to resist infections and hemorrhage. Oral infections increase the overall morbidity of cancer chemotherapy. If these infections are not discovered early and treated aggressively, they may be lethal following their systemic dissemination. Oral hemorrhaging may occur spontaneously and be profuse. Such incidents are terribly distressful to the patient, family and the professional care team. Fatal exsanguination has been reported.

Currently, antineoplastic drug therapy is being used with 40% of cancer patients either as a single treatment modality or as part of multi-modal therapy (chemotherapy, surgery, radiation). Some cancers respond well to single agent chemotherapy and others are treated with several agents in combination. New combinations and single agents are used in investigational clinical trials. The oral toxicity must be identified for all of these new agents and new combinations. Data show that nearly 50% of all individuals receiving chemotherapy will develop oral complication, most notably oral lesionary distinct in anatomical distribution and physical characteristics form other oral maladies resultant of fungal agents, bacteria and nutritional deficiencies. These complication include stomatitis, infection and hemorrhage Of this 50% incidence rate, 33% will develop one complication, 10% two complications and 3–4% will develop all three.

There is a plethora of scientific reports describing the multiple and varied oral complications as sequelae to cancer chemotherapy. Great detail has been used to describe these clinical entities. To a lesser degree, the scientific literature offers explanations for the pathogenesis of these oral lesions. Treatment protocols for these sequelae are more sparse and varied. Their development seems to be more empiric than scientific. An extensive literature search and a preliminary survey of some of the major cancer treatment centers in North America indicate that no treatment is presently available to prevent or significantly attenuate these oral complications. Clearly, there is a need for a proven, safe, comfortable and effective method and material to address this widespread and difficult problem.

SUMMARY OF THE INVENTION

The present invention seeks to overcome these and other drawbacks in the prior art by providing a chemically stable preparation adapted for prophylaxis and treatment of oral lesions. The claimed formulations include premixed forms of an oxidizing agent, such as hydrogen peroxide, benzoyl peroxide, and the like, and a source of bicarbonate, such as sodium bicarbonate, ammonium carbonate, or potassium carbonate. In one particularly preferred embodiment, the oxidizing agent, such as hydrogen peroxide, and the source of bicarbonate, such as sodium bicarbonate, are prepared together so as to form as premixed, aqueous solution.

The preparations of the present invention may alternatively be prepared in solid form so as to include the source of the peroxide, such as benzoyl peroxide, and source of bicarbonate, such as sodium bicarbonate, together in a dry or powder form, such as in a tablet. As a powder or tablet, benzoyl peroxide would be the preferred source of peroxide, together with a bicarbonate source, such as sodium bicarbonate. In such an embodiment, the dry powder or tableted mixture would be mixed in an appropriate volume of water or other carrier solution, such as water, saline or other mouth wash preparation, and allowed to form a liquid having the therapeutic concentrations of the bicarbonate and peroxide described herein.

In still another embodiment, the compositions of the present invention may take the form of a gel. Such may be accomplished, for example, through the use of gelling agents suitable for use in preparation of a gel containing a mixture of a peroxide and bicarbonate. Such a preparation may include, for example, flavoring agents and the like, and used as a gel in combination with a toothpaste. Alternatively, the gel may be formulated so as to be suitable for direct application to the gums.

Many sources of bicarbonate and peroxide are known to those of skill in the chemical arts, and the present invention is intended to encompass such functional equivalents suitable for use in the compositions of the present invention.

Techniques for preparing a powder, tablet, or gel are well known to those in the pharmaceutical arts, and therefore it is expected that the preparation of these alternative forms of the invention will be within the ordinary skill of one in these arts without any undue amount of experimentation. A text that outlines several of such standard techniques is Remington's Pharmaceutical Sciences (1990) (18th edition, Mack Publishing Company, Gennaro et al., editors). The relevant portions of this text are specifically incorporated herein by reference for these purposes.

Most surprisingly, premixed formulations provided in the present invention provide a therapeutically effective treatment for the prophylaxis and treatment of oral lesions. Premixed aqueous formulations which include a source of peroxide, such as hydrogen peroxide, and which are therapeutically effective for oral lesions, including non-bacterial lesions, is most surprising, as such sources as hydrogen peroxide are known to be particularly unstable in solution. This feature distinguishes the present invention from other preparations, as the therapeutic activity of the present compositions are surprisingly therapeutic even where the source of peroxide, such as hydrogen peroxide, is premixed in an aqueous solution with a bicarbonate source, such as sodium bicarbonate.

Typically, hydrogen peroxide solution has been used in the treatment of tissues of the oral cavity, where it is attacked by the enzyme catalase to provide the release of active oxygen. Hydrogen peroxide and sodium bicarbonate, together with table salt, have been used to destroy bacteria responsible for gum disease (Keyes procedure, substantially as described in S. Elder; "An Alternative to Gum Surgery" Modern Maturity, August–September 1980 pp. 31–32). However, the contact of these ingredients according to conventional practice, for example in the Keyes procedure, was prevented according to these techniques until application to the oral cavity in order to preserve the therapeutic value of the composition, described as particularly the release of active oxygen. Specifically, premixture of hydrogen peroxide and sodium bicarbonate is described in the literature as rendering the combination ineffective against gum disease. Devices have even been patented to prevent the premixture of hydrogen peroxide and sodium bicarbonate (U.S. Pat. No. 4,687,663).

Surprisingly, the present inventor has discovered that a premixture of a source of peroxide, such as hydrogen peroxide, in an aqueous solution, such as in combination with a solution of sodium bicarbonate, has not only a retained therapeutic activity, but also a profound therapeutic effect in healing oral lesions, particularly chemotherapeutic agent-induced oral lesions. Even more surprisingly, the inventor has found that the particularly described solutions of the present invention, particularly of sodium bicarbonate and hydrogen peroxide, may be used to effectively prevent the formation of oral lesions, including oral lesions in patients undergoing chemotherapy, by simple oral rinsing with the SOL solutions provided by the combination of peroxide and bicarbonate.

The inventor has also found that, contrary to conventional teachings in the art, a premixed formulation with a source of peroxide, such as hydrogen peroxide, with a source of bicarbonate, such as sodium bicarbonate, remains stable in the claimed concentration ranges over an extended period of time, and therefore has a much improved shelf-life. Such eliminates the necessity for such separate "compartmentalized" devices as described by Schaeffer et al. (U.S. Pat. No. 4,687,663), as well as the messy and inconvenient "dipped toothbrush-to-hand" system described in the Keyes procedure (substantially as described e.g. in S. Elder:"An Alternative to Gum Surgery," Modern Maturity, August/September 1980, pp. 31–32).

The therapeutic preparation of the present invention comprises a premixed formulation of water, a source of peroxide and a source of bicarbonate. In a most preferred embodiment, the premixed formulation includes between about 0.01% and about 0.8% hydrogen peroxide (most preferably 0.1% and 0.7%), and between about 0.01% and about 0.4% (most preferably 0.1% and 0.3%) sodium bicarbonate. To produce such a preparation adapted for the prophylaxis and treatment of oral lesions, most particularly those induced by chemotherapeutic agents, preferably involves mixing hydrogen peroxide and sodium bicarbonate to provide an aqueous solution having between about 0.01% and about 0.8% hydrogen peroxide and between about 0.01% and about 0.4% sodium bicarbonate. In more preferable embodiments of the present invention in an aqueous solution form, the hydrogen peroxide is included in an aqueous solution at a concentration of about 0.4% and the sodium bicarbonate is included at a concentration of about 0.2%

Amazingly, the premixed formulations of the invention with a source of peroxide, such as hydrogen peroxide, are found to be immensely valuable as both palliative agents and as a prophylactic regimen for a variety of non-bacterial oral pathologies, including stomatitis, gingivitis, candidiasis and, most particularly, those oral lesions incident chemotherapy.

Methods for prophylaxis and treatment of oral lesions are also included in the present invention. In one particular embodiment, the claimed method involves the step of initially providing a preparation preferably comprising water, a premixed aqueous solution of about 0.01% and about 0.8% hydrogen peroxide and between about 0.01% and 0.4% sodium bicarbonate. The source of peroxide, such as hydrogen peroxide, is thus presented in the formulation in a premixed form. Oral rinsing with said preparation, particularly multiple daily oral rinsing, is demonstrated to markedly enhance healing of oral lesions, as well as for impeding or preventing the development of oral lesions typically observed in patients being treated with a chemotherapeutic agent. Such chemotherapeutic agents are typically administered to patients as a treatment for cancer. Thus, the described methods and formulations may be most expeditiously employed for the treatment of oral lesions incident the use of chemotherapeutic agent.

In certain preferred embodiments, the preparation for prophylaxis and treatment of the present invention is defined further as comprising between about 20% and about 50% isotonic saline solution. In a preferred embodiment, the aqueous preparation of the present invention adapted for prophylaxis and treatment of oral lesions incident to cancer chemotherapy, comprise about 0.4% hydrogen peroxide, about 0.2% sodium bicarbonate and about 30% isotonic saline. In usage the preparation is used for oral rinsing on a daily multiple basis.

Upon mixture of the formulation ingredients, the formulation is most preferably to be stored in a light-impeding container. While not required, such will preserve the chemical nature of the mixture. The premixed formulation may be stored indefinitely without significant loss of therapeutic potency either at room temperature or refrigerated in a light impeding or other type of container.

Most preferably, the light-impeding container may, for example, be of an amber color, although any hue or color of light impeding container may be employed.

DESCRIPTION OF THE PREFERRED EMBODIMENT

The present invention discloses unique compositions, which include tablets, gels, and formulations, and methods of using same for the therapeutic treatment and prophylaxis of oral lesions. The formulation preferably comprises a premixed form of a source of peroxide and a source of bicarbonate, such as hydrogen peroxide or benzoyl peroxide, and sodium bicarbonate, in an aqueous solution. Alternative forms of the gel or tableted composition will be used, for example, as dissolved in water or other aqueous solution, to similarly provide the therapeutic composition. These tableted and gel forms of the invention provide products with an increased shelf-life that are quick and easy to prepare and use.

The formulation, otherwise referred to as SOL for purposes of the present invention, has been used to resolve, attenuate and prevent stomatitis in patients with solid and non-solid malignancies, all of which were treated with currently accepted chemotherapy protocols. Stomatitis is a reported significant side-effect in all of these treatment schedules. SOL not only performed well as a clinically effective agent for stomatitis but appeared to have a rather pronounced anti-plaque potential.

During the severe and prolonged myelosuppression following chemotherapy for leukemia, patients should not and did not, in the present studies, perform any dental flossing or tooth brushing. Oral physiotherapy abstinence is typically prescribed until the patients became hematologically stable so that flossing and tooth brushing would not produce any gingival hemorrhaging or life-threatening bacteremia/septicemia. Surprisingly, even without the attention of tooth brushing or flossing, the clinical crowns of the teeth, in these patients, remained clean and shiny during the severe neutropenic periods. None of the patients with natural dentition developed any significant gingival complications, such as gingivitis, *Candida albicans*, cheilitis, and aphthosis ulcer.

The presented examples involve patients subject to cancer chemotherapy as well as those suffering from stomatitis. Thus, the present oral lavage inventive treatment should have application for any individuals susceptible or subject to stomatitis-related oral lesions, as well as other pathologies of the oral cavity.

The following examples involving patients receiving chemotherapeutic agents are presented to describe preferred embodiments and utilities of the present invention and are not meant to limit the present invention unless otherwise stated in the claims appended hereto.

EXAMPLE 1

Standard Oral Lavage

Standard oral lavage (SOL) is a therapeutic oral rinse of the present invention that has been developed for individuals with oral soft tissue problems. These individuals are most clearly exemplified as medical oncology patients subject to chemotherapy who are likely to be the greatest beneficiaries of SOL treatment. SOL had its genesis from an understanding of oral physiology and alternations of this physiology during and after chemotherapy treatments.

In the preferred embodiment therapeutically utilized herein the following SOL was used.

200 ml 3% hydrogen peroxide
400 ml normal saline
800 ml sterile water
3360 mg sodium bicarbonate
Peppermint concentrate (to provide an acceptable flavor to the patient).

The formula was packaged in a clear 1-½ liter plastic jug, then inserted in an amber plastic bag for storage. The amber bag was to impede hydrogen peroxide from being deactivated by light. CEPACOL® may also be included as a flavoring agent so as to enhance patient compliance. Where CEPACOL® is desired as an ingredient, it may be added to the above formulation (about 100 ml CEPACOL® per 1½ liters of complete SOL).

So formulated, the SOL may be stored indefinitely with essentially no loss of therapeutic efficiency. The formulation may be stored at room temperature or refrigerated with equal clinical efficacy upon patient use.

Pertinent to a description of the clinical efficacy of (SOL) the following examples are summaries of three patients who were being subjected to chemotherapy. These patients responded favorably to SOL and developed minimal or no stomatitis.

EXAMPLE 2

M. J. was a 32 year old white female patient having a diagnosis of acute monocytic leukemia. She was treated with a standard remission-induction course of chemotherapy consisting of the following: Ara-C (170 mg per day) for seven days as a continuous intravenous infusion and Adriamycin (76 mg per day) for three days, intravenous push. She developed a severe stomatitis which required an intravenous morphine drip to manage pain.

There was severe ulceration of the labial and buccal mucous membranes which hemorrhaged sporadically and without provocation. The ventral surfaces of the tongue and the anterior floor of the mouth were similarly involved. Crenation of the tongue, due to fluid retention, produced additional traumatic ulcerations of its periphery from the base on the right side circumferentially to the left base. The uvula, soft palate, tonsillar pillars and the posterior oropharynx had multiple ulcerative lesions. Many of these oral lesions presented with pseudomembranes. Gingival hemorrhaging was bothersome at times. *Candida albicans* became a complicating component as an opportunistic infection.

SOL was minimally used as an oral rinse every two hours while the patient was awake and twice during the night. M. J. was instructed to rinse with two to three ounces of SOL as descried above and more frequently, if desired. A topical antifungal rinse was employed following meals and at bedtime to prevent and treat Candida. Candida is a fungal infection which is unrelated to the direct effects of the chemotherapeutic agents being administered to the patient.

Most surprisingly, through the use of SOL and careful clinical surveillance, the patient's initial severe stomatitis was resolved in six days during a period of pancytopenia. Since the remission-induction chemotherapy the patient received seven more courses of induction and consolidation chemotherapy. Several of these courses were high dose Ara-C and L-asparaginase. The only oral reaction noted was with the sequential high dose Ara-C courses of a one week duration. With this therapy, accompanied by SOL treatment, one oral ulcer developed with each week of treatment; the ulcer measuring about one millimeter in diameter. The patient was free from any other oral pathology.

EXAMPLE 3

Another patient was W. W., a 49 year old white male with advanced colorectal cancer. This patient, with Duke's classification C adenocarcinoma of the rectum, was treated surgically with post-operative radiotherapy. Recurrence of this cancer was managed with high dose 5-fluorouracil administered as continuous intravenous infusion for five days. This regimen produced a moderately severe stomatitis that involved the labial and buccal mucosae and the latero-ventral surfaces of the tongue. It must be noted that this patient had multiple missing and curiously diseased teeth. Periodontally, these teeth showed significant bone loss.

Treatment of this 5-fluorouracil-induced stomatitis was performed with SOL in the same protocol described in Example II. Subsequent courses of 5-fluorouracil were administered to this patient using the identical dose and route of administration but accompanied with SOL therapy and no stomatitis was found to develop with steadily increasing CEA levels.

Patient W. W. was not totally compliant with the oral care and smoked rather heavily, typically two to three packs of cigarettes (Camels) per day. Tooth brushing and the use of dental floss were never part of the patient's health habits.

EXAMPLE 4

Another patient, J. L., was a 23 year old white male with a diagnosis of acute myeloblastic leukemia. This patient received a standard remission-induction chemotherapy regimen consisting of the following: Ara-C (190 mg per day) for seven days as a continuous intravenous infusion and Daunomycin (85 mg per day) for three days intravenous push.

As this chemotherapy quite consistently produces stomatitis, the patient was managed with the SOL protocol described in Example III. Only slight inflammation of the maxillary facial posterior gingivae on the left was noted. No oral ulcerations were seen. There were numerous consolidation treatments with m-AMSA/Ara-C and Ara-C/Daunomycin. Several of these regimen were high dose. No stomatitis developed in this patient during or after these treatments.

EXAMPLE 5

The present example is provided to demonstrate the therapeutic action of the various combinations of hydrogen peroxide ($H_2O_2$), sodium chloride (NaCl), and sodium bicarbonate ($NaHCO_3$) as compared to the relative ineffective therapeutic value of solutions which include only one of these ingredients in the treatment and prevention of oral ulcers, particularly those oral lesions manifest in patients exposed to orally toxic chemotherapeutic agents.

The following solutions were employed in the study:

| Ingredient | Solution 1 | Solution 2 | Claimed Solution - Solution 3 |
|---|---|---|---|
| NaCl | <1% | <1% | <1% |
| $H_2O_2$ | 3% | — | 0.4% |
| $NaHCO_3$ | — | 0.2% | 0.2% |
| patient # oral lesions prevented | 0/18 = 0% | 0/29 = 0% | 16/16 = 100% |

The Solution #3 of hydrogen peroxide and sodium bicarbonate was prepared as a premixed solution and stored in an amber bottle until use.

Each patient from each of the respective groups rinsed with their respective oral lavage three times a day. All patients in each of the groups were receiving a chemotherapeutic agent associated with the development of stomatitis. The object of the oral lavage treatment was to achieve prevention of stomatitis in patients who had a prior history of having developed oral lesions after previous courses of treatment with chemotherapeutic agents. The oral lavage was also evaluated for its ability to decrease the duration of stomatitis and promote healing of the ulcerations.

The data collected from these studies indicates that solution of hydrogen peroxide alone (Solution 1 - 3% $H_2O_2$) or sodium bicarbonate alone (Solution 2 - 0.2% NaHCO3) were ineffective for preventing the oral lesions incident chemotherapy treatment demonstrated by patients after prior chemotherapeutic treatments with no oral lavage. In contrast, patients demonstrating a prior history of chemotherapeutic-agent induced oral lesions after chemotherapeutic agent treatment who instead were treated with an oral lavage of a premixed formulation of hydrogen peroxide and sodium bicarbonate (3% $H_2O_2$+2% sodium bicarbonate) were effectively protected against the formation of oral lesions in all patients tested (16 out of 16 patients tested).

These data demonstrate that while a solution of hydrogen peroxide or sodium chloride alone are ineffective for preventing chemotherapeutic-agent induced oral lesionary, a premixed solution containing a mixture of both hydrogen peroxide and sodium bicarbonate, hydrogen peroxide thus being included in its chemically treated form, effectively prevented the development of oral lesionary previously observed in patients after having received chemotherapeutic agent in prior treatments. This result is surprising and most unexpected, as the mixture of hydrogen peroxide and sodium bicarbonate produces an immediate reaction, rendering the premixed solution, as per prior reports employing the Keyes procedure, therapeutically ineffective (See S. Elder (August–September 1980) Modern Maturity, pp. 31–32).

These results also demonstrate that the mixture of sodium bicarbonate with hydrogen peroxide does not reduce the effectiveness of the resulting premixed solution against preventing the particular and unique type of oral lesions incident the chemotherapy treatment of a patient.

EXAMPLE 6

SOL Prolonged Therapeutic Effectiveness

The present example is provided to demonstrate the prolonged stability and therapeutic effectiveness of the claimed formulation against oral lesions. The formulations were found to remain therapeutically effective up to 3 weeks after mixture in an aqueous solution. In addition, the presently described premixed formulation may be used to relieve xerostomia (dryness of the mouth), so as to increase oral hydration of the mouth as well as in the treatment of oral candidiasis, as well as for the debridement and cleaning of the oral soft tissues and mucus membranes. Use of the present formulations as an oral lavage manifests an elevation in the pH of the oral environment beyond the immediate time after oral rinsing, for at least ½ hour or more.

The formulation has also been observed to reduce the amount of plaque formation as well as retard the initial formation of plaque on tooth surfaces.

An oral lavage was formulated in a single batch of 1 liter according to the formula described in Example 1. The premixed hydrogen peroxide and sodium bicarbonate was then stored in a 1½ liter amber colored container at room temperature.

Patient V. F. (adult, female, 76 years of age) presented with a severe case of stomatitis, and was initiated on a four-times-daily oral treatment regimen with the described oral lavage. The patient was instructed not to eat or drink anything for 30 minutes after each treatment. The same batch of oral lavage was used over a three week treatment period, stored at room temperature near the patient's bedside.

V. F. developed stomatitis through a rather common set of circumstances seen in older adults. She suffered chronically from degenerative hip joint disease which produced continuous pain and dysfunctional ambulation. It became necessary to perform surgery where a prosthetic total hip joint was placed. Subsequent to this surgery, V. F. required significant doses of analgesic medications for pain during her rehabilitation process for the hip replacement prosthesis. Marked xerostomia (mouth dryness) was the major side effect of the analgesics which produced excessive oral mucosal friction, decreased oral pH and the resultant stomatitis. After 3 days of SOL (4× daily, as described), the stomatitis showed resolution and by day 5 was completely resolved. SOL therapy was continued for about 3 weeks as the dosage of analgesic medication was significantly reduced over this period of time. Stomatitis was resolved and subsequently resolved from reoccurring using the described SOL regimen.

Initial solution of SOL kept at her bedside first 2 weeks in an amber bag. Subsequent formulations of the SOL were prepared. Patient V. F. used approximately 120 ml day of the SOL. Thus, a 1 liter batch is about a 2-week supply Stomatitis results in dryness of the mouth and logarithmic loss of salivary buffering capacity (i.e., pH 7 to 6 for example is a 10-fold reduction). An extreme decrease in pH therefore results with this condition, wherein the oral cavity becomes extremely acidic.

The patient's oral stomatitis condition was observed to improve steadily with each treatment. The stomatitis was virtually eliminated upon the 3rd week of treatment.

The results observed demonstrate that the disclosed formulation, with its premixed forms of hydrogen peroxide and sodium bicarbonate, provide a pharmacologically active preparation effective for the treatment of oral pathologies.

EXAMPLE 7

Preparation of Bicarbonate and Peroxide in Powder or Tablet Form

The present example provides the description of a powder that includes a source of peroxide, such as benzoyl peroxide, together with a source of bicarbonate, such as sodium bicarbonate. This powder may then be mixed with an appropriate quantity of water or other aqueous carrier so as to form a liquid that may then be easily used by the patient as a mouth rinse, medicament or to promote general oral health.

Powdering and tableting techniques are well known to those of skill in the art, as evidenced by the several protocols described in Remington's Pharmaceutical Sciences (18th edition, 1990). This reference is specifically incorporated herein in pertinent part for this reason.

Alternatively, the composition may be formulated into a tablet. To provide the solid or dry composition for the tableting process, a quantity of sodium bicarbonate peroxide crystals (see the Merck Index, 11th Edition, 1989, p. 1124, #1128), dibenzoyl peroxide), may be admixed together with a tableting agent. The concentration of each ingredient in the tablet will be such that, when dissolved in a volume of water (preferably one cup), a liquid containing therapeutically effective concentrations of the bicarbonate and peroxide will be formed. These therapeutically effective concentrations are about between 0.01% and about 0.8% peroxide, preferably between 0.1 and about 0.8%, using, for example, benzoyl peroxide, and between about 0.01% and about 0.4% bicarbonate, preferably between 0.1% and about 0.4%, using for example, as sodium bicarbonate or urea bicarbonate.

EXAMPLE 8

Preparation of a Bicarbonate and Peroxide Gel

The present example describes the preparation of the present invention as contemplated in the form of a gel that includes both a source of bicarbonate, such as sodium bicarbonate, and a source of peroxide, such as benzoyl peroxide or hydrogen peroxide.

An advantage of the combination gel of the invention stems from the tendency of a gel to cling to the gum tissues, and thus provide them with the full benefit of substantially all of the composition applied to the gums.

Gelling agents suitable for use in preparation of the peroxide and bicarbonate gel in accordance with this invention should be nontoxic and neutral to the peroxide to assure its stability. In addition, they should be preferably sensitive to external electrolytes. A gelling agent suitable for use with the present invention is a copolymer of acrylic acid cross-linked with polyallyl sucrose, as described in U.S. Pat. No. 2,798,053 issued on Jul. 2, 1957 and assigned to B.F. Goodrich Inc. Other gelling agents resulting in stable hydrogen (or urea) peroxide and bicarbonate gels suitable for use in the present invention include those described in British Pat. No. 827,331, i.e., organic polymeric acid colloids including polyuronic acids, carboxypolymethylene compounds and polyester resins containing three carboxyl groups, such as partially hydrolized polyacrylates or polymethacrylates and copolymers thereof; and those described in U.S. Pat. No. 3,639,574 issued on Feb. 1, 1972 to Schmolka, i.e., polyoxyethylene polyoxypropyleneblock copolymers, which, according to Schmolka, may be used in the preparation of stable, firm peroxide gels. Preferred are water-dispersible copolymers of acrylic acid cross-linked with about 0.75 to about 1.5\5 of polyallyl sucrose and neutralized with triethanolamine, NaOH or another alkalizing agent, as taught in U.S. Pat. No. 3,499,844[1] issued on Mar. 10, 1970 to Kibbel et al. For purposes of the present invention, Kibbel's acrylic copolymer may be preferably combined with an anionic or non-ionic surfactant, such as disclosed in U.S. Pat. No. 4,130,501[2] issued on Dec. 19, 1978 to Lutz et al. Such surfactants are not essential for the formation of a stable hydrogen peroxide gel in accordance with this invention, but may be added to facilitate distribution and rapid penetration of the composition throughout the area to be treated. A particularly preferred gelling agent for the purposes of the present invention is that described by Kibbel, supra. This gelling agent may but does not have to be modified by the addition of a suitable amount of non-ionic cellulose gum such as hydroxyethyl- or hydroxypropyl-cellulose or hydroxypropyl-methyl-cellulose in order to improve the physical stability of the gel, especially when subjecting it to stress such as that resulting from squeezing of the gel through a tube, or pumping action.

[1] The disclosures of these patents are incorporated herein by reference.
[2] The disclosures of these patents are incorporated herein by reference.

The most preferred gelling agents are marketed under the trademark CARBOPOL 941 or 1342 (an acrylic acid copolymer) by Goodrich. Carbopol 941 does not need neutralization for gelling (and preferably is not neutralized in this invention) because it gels readily in the presence of hydrogen donors. Carbopol 941 has proved to have greater long term physical stability (also believed to be due to hydrogen bonding). Carbopol 1342 is described by the manufacturer to display satisfactory long term stability comparable to that of Carbopol 941, even though it needs to be neutralized.

Gels made from these agents do not need any cellulose additive as a stabilizer, because they are thixotropic (and also pseudoplastic).

Not only is Carbopol 941 the most preferred gelling agent for non-neutralized gels, it is also most preferred for neutralized gels along with Carbopol 934, 940 and 1342.

The peroxide and bicarbonate gel of the invention may contain the following ingredients in the following amounts:

$H_2O_2$: about 0.01–0.8% and preferably about 0.01–0.05% (or 0.1% to about 0.2%);

sodium bicarbonate: 0.01–0.4%;

flavoring agent(s): to taste, preferably 0.1–2%.

Preferably, a range of about 0.01–0.05% sodium bicarbonate is included in the gel. Alternatively, benzoyl peroxide may be used instead of hydrogen peroxide, preferably at near the same relative concentrations.

In order to disperse the "chalky" taste imparted mostly by a bicarbonate, a bodying agent is added, such as sorbitol, glycerin and/or a glycol. In addition, if the gel is to displace toothpaste completely, additional cleansing agents, such as calcium sulfate, calcium phosphate, hydrated aluminum oxide, calcium carbonate, magnesium carbonate, and magnesium silicate or mixtures thereof can be added. A fluorine-containing compound is also preferably included for its anti-caries activity. Suitable fluorine-containing compounds are NaF, Na-monofluorophosphate, KF, potassium monofluorophosphate, sodium fluorosilicate, sodium fluorozirconate, etc. (with NaF being most preferred. Finally, a foaming agent such as sodium lauryl sulfate (most preferred), sodium N-lauroyl sarcosinate, sodium coconut monoglyceride sulfonate, sodium N-methyl-N-palmitoyl lauride or a nonionic surfactant such as a polysorbate (e.g. Tween 60 or 80 manufactured by ICI Americas, Wilmington, Del.) or poloxamer or mixtures thereof, may be added.

Flavoring agents, such as sodium saccharin, or other artificial sweeteners, peppermint or spearmint or other flavors are preferably added to further curb the unpleasant taste of the gel tablet, or aqueous solution formulations of the presently defined compositions. Finally, methyl, butyl and/or propyl paraben, sodium benzoate, potassium sorbate or mixtures thereof may be added as preservatives, with methyl and propylparaben being most preferred. Use of a coloring agent is optional.

The gels thus include both a source of bicarbonate and a source of peroxide. The source of peroxide may comprise urea peroxide, hydrogen peroxide, or benzoyl peroxide, or other like compositions well known to those of skill in the art.

The combination gel of peroxide and bicarbonate may then be contained with a single tube or pump, such as a toothpaste tube, for convenient use.

The phrase "pharmaceutically acceptable" refers to molecular entities and compositions that do not produce an allergic or similar untoward reaction when administered to a human.

Upon formulation, solutions will be administered in a manner compatible with the dosage formulation and in such amount as is therapeutically effective. The formulations may be easily administered in a variety of dosage forms. Some variation in dosage will necessarily occur depending on the condition of the subject being treated, and the progression and rate of dissipation of the disease. The person responsible for administration will, in any event, determine the appropriate dose for the individual subject.

Changes may be made in the elements and components described herein or in the steps or the sequence of steps of the method described herein without departing from the concept and scope of the invention as defined in the following claims.

What is claimed is:

1. A premixed pharmaceutical composition of the treatment of oral lesions consisting essentially of therapeutic levels of hydrogen peroxide and sodium bicarbonate in an aqueous solution.

2. An oral lavage preparation for prophylaxis and treatment of oral lesions, the preparation consisting essentially of a premixed solution of water, isotonic saline and hydrogen peroxide, and sodium bicarbonate at therapeutically effective levels.

3. A method for prophylaxis or treatment of oral lesions in a patient, the method comprising the steps of:

preparing a premixed aqueous formulation consisting essentially of hydrogen peroxide, and sodium bicarbonate at therapeutically effective levels and isotonic saline; and orally rinsing a patient having or at risk of developing oral lesions with the premixed formulation.

4. The method of claim 3 wherein the oral lesions are induced by a chemotherapeutic agent.

5. A method for the treatment of chemotherapeutic agent-induced oral lesions, the method comprising:

treating a patient having chemotherapeutic agent-induced oral lesions with a premixed solution consisting essentially of therapeutically effective levels of hydrogen peroxide and sodium bicarbonate.

6. An oral lavage for prophylaxis of chemotherapeutic agent-induced oral lesions, the oral lavage consisting essentially of an aqueous and stable premixture of solution, of hydrogen peroxide and sodium bicarbonate at prophylactically effective levels.

7. The oral lavage of claim 6 wherein the solution is between about 20% and about 50% isotonic saline solution.

8. The oral lavage of claim 6 defined further as comprising ethyl alcohol.

9. The method of claim 3 or claim 5 wherein the oral lavage is defined further as containing between about 20% and about 50% isotonic saline solution.

10. The method of claim 3 or claim 5 wherein the oral lavage is defined further as containing about 0.4% hydrogen peroxide.

11. The method of claim 3 or claim 5 wherein the oral lavage is defined further as containing about 0.2% sodium bicarbonate.

12. The method of claim 5 wherein the chemotherapeutic agent-induced oral lesion is induced by the chemotherapeutic agent methotrexate, 5-fluorouracil, Ara-C, cis-platinum, m-AMSA, daunorubicin, bleomycin, cytosine arabinoside or a mixture thereof.

* * * * *

UNITED STATES PATENT AND TRADEMARK OFFICE
CERTIFICATE OF CORRECTION

PATENT NO. : 5,540,913

DATED : July 30, 1996

INVENTOR(S) : Robert E. Turner

It is certified that error appears in the above-identified patent and that said Letters Patent is hereby corrected as shown below:

Claim 1, column 12, line 16, delete "of" and insert --for-- therefor.

Signed and Sealed this

Twelfth Day of November, 1996

Attest:

BRUCE LEHMAN

Attesting Officer     Commissioner of Patents and Trademarks